(12) United States Patent
Matsumoto

(10) Patent No.: US 8,506,081 B2
(45) Date of Patent: Aug. 13, 2013

(54) OPHTHALMIC IMAGE SENSING APPARATUS

(75) Inventor: Kazuhiro Matsumoto, Tochigi-ken (JP)

(73) Assignee: Canon Kabushiki Kaisha, Tokyo (JP)

( * ) Notice: Subject to any disclaimer, the term of this patent is extended or adjusted under 35 U.S.C. 154(b) by 366 days.

(21) Appl. No.: 11/781,767

(22) Filed: Jul. 23, 2007

(65) Prior Publication Data

US 2008/0018854 A1     Jan. 24, 2008

Related U.S. Application Data

(63) Continuation of application No. 11/233,628, filed on Sep. 22, 2005, now Pat. No. 7,347,553.

(30) Foreign Application Priority Data

Sep. 24, 2004   (JP) ................................ 2004-276724
Oct. 15, 2004   (JP) ................................ 2004-300968

(51) Int. Cl.
    *A61B 3/10*      (2006.01)

(52) U.S. Cl.
    USPC .......................................... 351/214; 351/205

(58) Field of Classification Search
    USPC ................... 351/205, 206, 214, 246
    See application file for complete search history.

(56) References Cited

U.S. PATENT DOCUMENTS

| | | | | |
|---|---|---|---|---|
| 4,469,416 A | * | 9/1984 | Isono ............................. | 351/206 |
| 4,533,221 A | | 8/1985 | Trachtman | |
| 4,755,041 A | | 7/1988 | Ishikawa et al. | |
| 5,066,117 A | * | 11/1991 | Matsumura ................... | 351/226 |
| 5,163,437 A | * | 11/1992 | Fujii et al. ..................... | 600/476 |
| 5,371,557 A | | 12/1994 | Nanjho et al. | |
| 5,455,644 A | * | 10/1995 | Yazawa et al. ................ | 351/206 |
| 2004/0169818 A1 | * | 9/2004 | Hoshino ....................... | 351/205 |
| 2004/0252276 A1 | * | 12/2004 | Nanjo et al. .................. | 351/206 |

FOREIGN PATENT DOCUMENTS

| | | |
|---|---|---|
| JP | 51-137413 | 11/1976 |
| JP | 52-142895 A | 11/1977 |
| JP | 54-054494 | 4/1979 |
| JP | 60-060831 | 4/1985 |
| JP | 01-178258 | 7/1989 |
| JP | 5-023306 A | 2/1993 |
| JP | 05-095902 | 4/1993 |
| JP | 06-142050 | 5/1994 |
| JP | 06-217941 | 8/1994 |
| JP | 08-033610 | 2/1996 |
| JP | 08-150121 | 6/1996 |
| JP | 09-271464 | 10/1997 |
| JP | 2000-116603 A | 4/2000 |
| JP | 2002-065611 A | 3/2002 |

* cited by examiner

*Primary Examiner* — James Greece
(74) *Attorney, Agent, or Firm* — Carter, DeLuca, Farrell & Schmidt LLP

(57) ABSTRACT

A focusing unit (11) is constituted of a prism base (11a), deflection prisms (11b and 11c), and a slit chart (11e) having a slit opening (11d), and the deflection prisms (11b and 11c) are arranged so that deflecting directions may become reverse. The slit opening (11d) is made equally to spread across the deflection prisms (11b and 11c) approximately and is impermeable except the slit opening (11d), and light incident on the deflection prisms (11b and 11c) passes only this slit opening (11d). In addition, the light which is emitted by a focus index illumination light source illuminates the slit opening (11d) through the deflection prisms (11b and 11c). As to an image of the illuminated slit opening (11d), two slit images are formed on a fundus of eye by actions of the deflection prisms 11b and 11c. Focus adjustment is made by aligning these slit images (S1 and S2) in a straight line.

19 Claims, 12 Drawing Sheets

OPHTHALMIC IMAGE SENSING APPARATUS

This is a continuation of prior application Ser. No. 11/233,628, filed Sep. 22, 2005, which is hereby incorporated by reference in its entirety as if fully set forth herein.

This application claims priority from Japanese Patent Application Nos. 2004-276724 filed on Sep. 24, 2004 and 2004-300968 filed on Oct. 15, 2004, which are hereby incorporated by reference herein.

BACKGROUND OF THE INVENTION

1. Field of the Invention

The present invention relates to an ophthalmic image sensing apparatus used in an opthalmologist's office etc.

2. Related Background Art

Up to now, in fundus cameras, what are disclosed in Japanese Patent Application Laid-Open No. H05-095902, Japanese Patent Application Laid-Open No. H08-033610, and Japanese Patent Application Laid-Open No. H08-150121 are methods of providing a mechanism of providing a focus index projection barrel which is constituted of an index for focusing detection, a light source illuminating this index, and a projection optical system which has a deflection prism for projecting index images on a fundus of an eye to be examined from different locations of a pupil, and a micro mirror which branches an optical path with a fundus illumination optical system, and of both the micro mirror and focus index projection barrel moving in a direction of an optical axis with interlocking with the focus adjustment of an image sensing optical system, and a mechanism of the micro mirror retreats out of the optical path at the moment of image sensing, and of focusing the fundus of eye with looking at the index images projected on the fundus of eye.

In addition, methods of providing a minute prism in an illumination optical system, projecting a slit image illuminated by fundus observation light on the fundus of eye, and performing focus adjustment are disclosed in Japanese Patent Application Laid-Open No. H06-142050 and Japanese Patent Application Laid-Open No. S54-054494.

Since the above-mentioned conventional methods each must move a whole focus index projection barrel, which is provided with being branched from a fundus illumination optical system, in a direction of an optical axis, it is necessary to secure a large space, and hence, it is difficult to downsize an apparatus. In addition, there are problems that cost is high because of necessity of long adjustment time due to a large parts count, and assembly operation, such as angle adjustment of a micro mirror, and alignment between an index image and a micro mirror, is complicated. Furthermore, there is another problem that a slack wire is worn because the light source where wires are connected is moved.

Moreover, the method of providing a minute prism in the above-mentioned illumination optical system has a problem that it is hard to perform focus adjustment since a focus index portion becomes darker than a surrounding fundus region because of decentering the fund illumination light by a prism and projecting a focus index, or it is user-unfriendly since it is not possible to adjust light intensity independently because fundus illumination and focus index illumination are performed by one light source.

In addition, in fundus image sensing in a mass health examination, an examinee's look is adjusted and image sensed so that a just middle position between an optic disk and a yellow spot may become a center of a screen. Hence, it is necessary to guide this yellow spot in a position, which is decentered from an optical axis, and to take a picture. Nevertheless, it is necessary to change a position of a fixation target at the time of taking a picture of a right eye and at the time of taking a picture of a left eye since the structure of fundi of the right and left eyes is left-right symmetric.

Hence, in fundus cameras, as disclosed in Japanese Patent Application Laid-Open No. S60-060831, Japanese Patent Application Laid-Open No. H06-217941, and Japanese Patent Application Laid-Open No. H09-271464, it has been performed up to now to present to a person to be examined a fixation target according to right and left eyes by providing an optical path which branches from an image sensing optical system, providing a plurality of light sources in conjugation positions with an image sensing plane in the optical path as fixation targets, and turning on the light sources selectively. Since image sensing light and a fixation target are visible light, a flip-up mirror, a half-mirror, or the like which branches an optical path is used.

In addition, what is also known is a method of Japanese Patent Application Laid-Open No. S51-137413 of arranging detachably a light source in an illumination optical system, and presenting a fixation target.

However, in the above-described conventional methods, there are problems that an optical system becomes large because of providing a branch optical path, and that a mechanism becomes complicated in the case of using a flip-up mirror, or a light source with a larger volume is needed since a utilization efficiency of light intensity falls in the case of using a half-mirror, and further, the dazzle of a person to be examined increases.

Furthermore, the method of arranging a light source as a fixation target in an illumination optical system has a problem that the image quality of a fundus observation image deteriorates since illumination unevenness arises because fundus illumination light is disturbed by parts for supporting the light source, the light source itself, a cable, and the like.

SUMMARY OF THE INVENTION

The present invention aims at solving the above-described subjects, and providing an ophthalmic image sensing apparatus which makes it possible to obtain a fundus image with good image quality without illumination unevenness.

An ophthalmic image sensing apparatus according to one aspect of the present invention for attaining the above-mentioned object has the following structure.

Namely, the ophthalmic image sensing apparatus has:

a fundus image sensing optical system for sensing an image of a fundus of eye to be examined;

focus adjustment means of adjusting a focus of the above-mentioned fundus image sensing optical system;

an illumination optical system for illuminating the above-mentioned eye to be examined;

a perforated mirror which branches an optical path into an optical path of the fundus image sensing optical system, and an optical path of the above-mentioned illumination optical system;

first and second relay lenses having focal points near an opening of the above-mentioned perforated mirror;

a slit index of being arranged between the first and second relay lenses, and its image being projected on the above-mentioned fundus of eye;

a deflection prism arranged around the slit index;

a focusing unit movable in a direction of an optical axis with interlocking with the above-mentioned focus adjustment means;

a light shielding member arranged in an approximately focal position of the above-mentioned second relay lens; and illumination means of illuminating the above-mentioned slit index.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

The accompanying drawings, which are incorporated in and constitute a part of the specification, illustrate embodiments of the invention and, together with.

DETAILED DESCRIPTION OF THE PREFERRED EMBODIMENTS

Preferred embodiments of the present invention will now be described in detail in accordance with the accompanying drawings.

The present invention will be described in detail on the basis of embodiments shown.

First Embodiment

Figure 1:
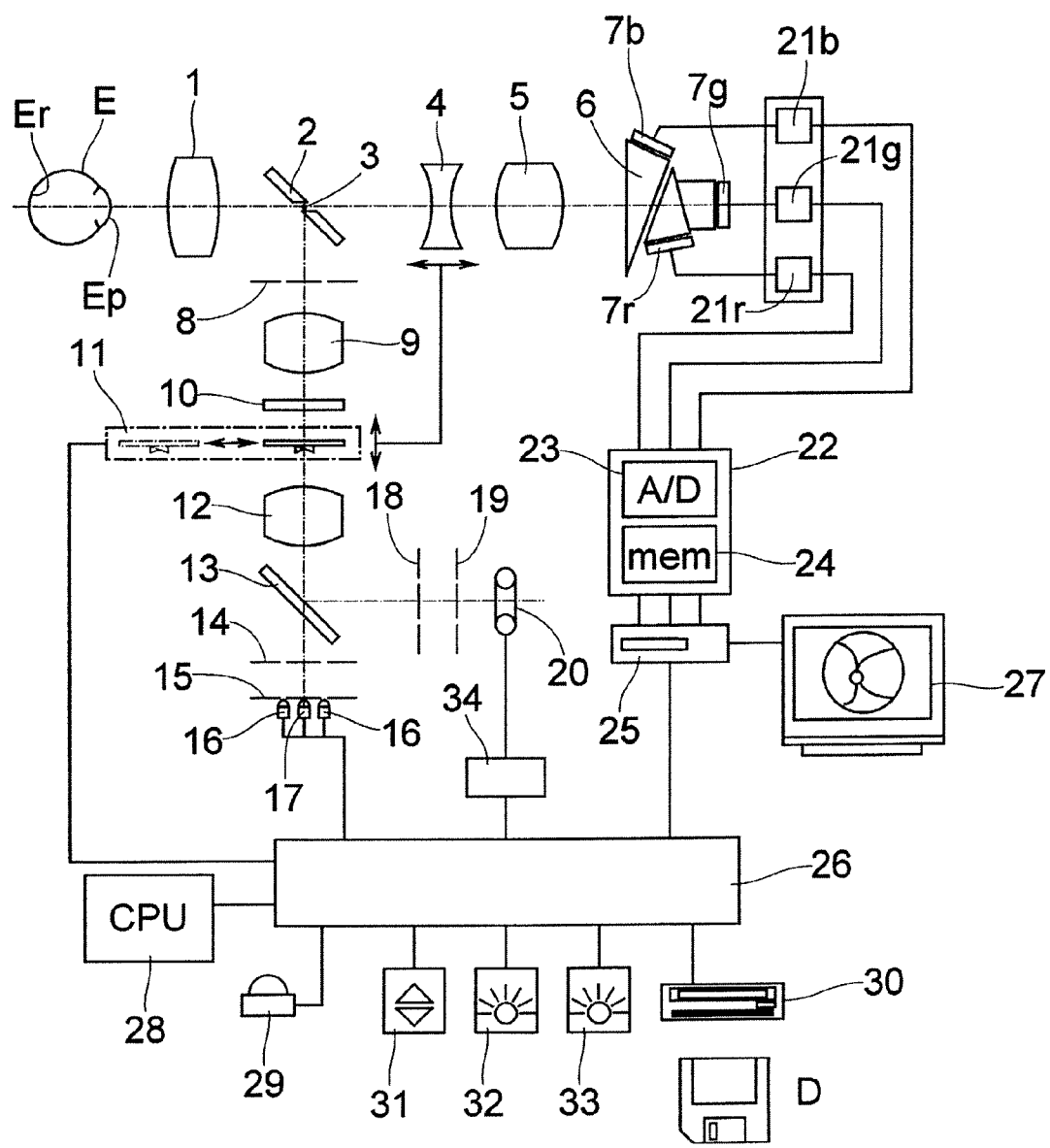
FIG. 1 is a structural diagram of a fundus camera of a first embodiment.

FIG. 1 is a structural diagram of a fundus camera of this embodiment. Fundus examination and sensing means has the structure that an image sensing mechanism comprising an objective lens 1, a perforated mirror 2, an image sensing diaphragm 3 arranged inside an opening of this perforated mirror 2, a focus lens 4, an image sensing lens 5, a color separation prism 6, and image sensing devices 7r, 7g and 7b is arranged in front of an eye E to be examined.

Figure 2:
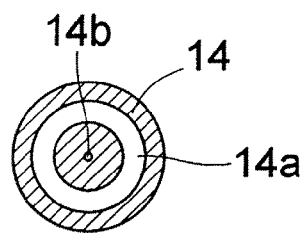
FIG. 2 is a front elevation of a crystalline lens diaphragm.
Figure 3:
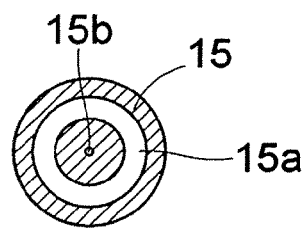
FIG. 3 is a front elevation of a ring diaphragm.
Figure 4:
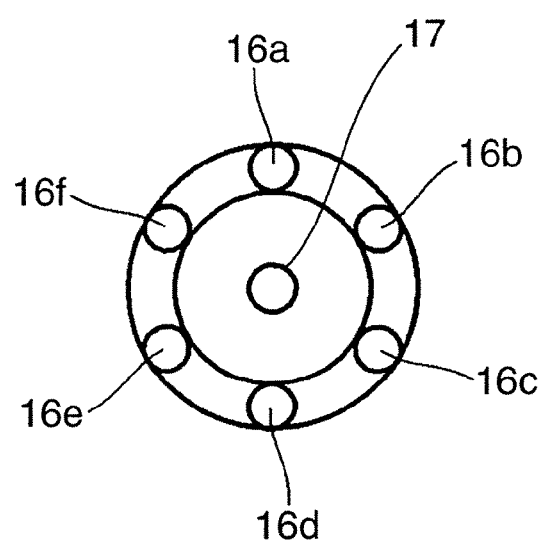
FIG. 4 is an explanatory drawing of arrangement of an observation light source and a focus index illumination light source.

What are arranged in the fundus illumination system located in an incident direction of the perforated mirror 2 are in view of the perforated mirror 2 a cornea diaphragm 8 having a ring-like opening projected near a cornea, a first relay lens 9, a black spot plate 10 on which black spots for removing reflection by the objective lens 1 are formed near an optical axis, a focusing unit 11 which has a prism and a focus index, moves in a direction of the optical axis with interlocking with the focus lens 4, and retreats out of an optical path at the time of still image sensing, a second relay lens 12, an optical path branching mirror 13 which reflects visible light and transmits infrared light, a crystalline lens diaphragm 14 which has a ring-like opening 14a projected near a rear surface of a crystalline lens of an eye to be examined, has a small opening 14b in a center portion, and is shown in FIG. 2, a ring diaphragm 15 which has a ring-like opening 15a projected near a pupil Ep of the eye E to be examined, and id shown in FIG. 3, a plurality of observation light sources 16a to 16f which consist of LEDs, which emit infrared light, and are arranged circumferentially as shown in FIG. 4, and a focus index illumination light source 17 arranged in a central portion.

A crystalline lens diaphragm 18 having a ring-like opening projected near the rear surface of a crystalline lens of an eye to be examined, a ring diaphragm 19 having a ring-like opening projected near the pupil of the eye E to be examined, and a sensing light source 20 are arranged in a reflecting direction of the optical path branching mirror 13.

The image sensing diaphragm 3 in the opening of the perforated mirror 2 is located in an approximately focal position of the first relay lens 9. In addition, the diaphragm 15 and diaphragm 19 are arranged in an approximately focal position of the second relay lens 12. Furthermore, the ring-like opening 15a of the ring diaphragm 15 is illuminated by the illumination light sources 16a to 16f. The small opening 15b is illuminated by the index illumination light source 17.

Figure 5:
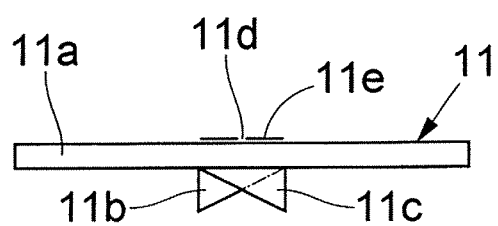
FIG. 5 is a sectional view of a focusing unit.
Figure 6:
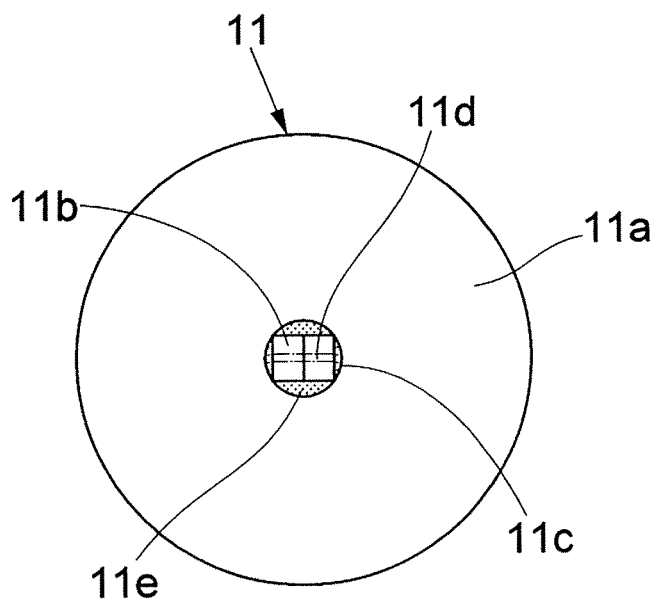
FIG. 6 is a plan view of the focusing unit.
Figure 7:
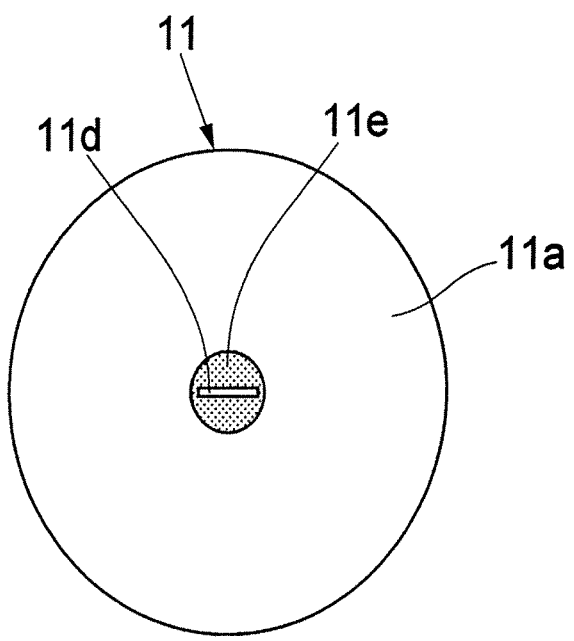
FIG. 7 is a rear view of the focusing unit.

The focusing unit 11 is constituted of a prism base 11a, deflection prisms 11b and 11c, and a slit chart 11e having a slit opening 11d, as shown in a sectional view of FIG. 5. As shown in FIG. 6, the deflection prisms 11b and 11c are arranged in a central portion of the prism base 11a so that deflecting directions may become reverse directions. In addition, the slit chart 11e is arranged in a central portion of the prism base 11a, and the slit opening 11d is arranged so as to spread across the deflection prisms 11b and 11c approximately equally, as shown in FIG. 7. Since portions except the slit opening 11d of the slit chart 11e are impermeable, light incident into prism portions passes only this slit opening 11d.

Each output of the image sensing elements 7r, 7g, and 7b is connected to an image board 22 through amplifying circuits 21r, 21g, and 21b. The image board 22 has an A/D converter 23 and memory 24. Further, an output of the image board 22 is connected to image control means 25, a television monitor 27, and a system bus 26. What are connected to the system bus 26 are a CPU 28, a sensing switch 29, recording means 30, a focus switch 31, an observation light intensity adjustment knob 32, a focus index brightness adjustment switch 33, and a drive circuit 34 of the sensing light source 20.

In order to sense a fundus image of a person to be examined using this fundus camera, a camera person sits the person to be examined in front of the fundus camera, and performs the alignment of an eye E to be examined and the fundus camera, and focusing, with observing moving images of a fundus Er of the eye E to be examined.

In the focusing, infrared light emitted by the observation light sources 16a to 16f passes through the ring-like opening 15a of the ring diaphragm 15, and the ring-like opening 14a of the crystalline lens diaphragm 14, and permeates the optical path branching mirror 13. Further, the infrared light passes through the second relay lens 12, focusing unit 11, black spot plate 10, first relay lens 9, and opening of the cornea diaphragm 8, and is reflected toward the left by the perforated mirror 2 to illuminate the fundus Er of eye through the pupil Ep of the eye E to be examined through the objective lens 1. An image of the fundus Er of eye illuminated in this way passes through the objective lens 1, image sensing diaphragm 3, focus lens 4, and image pickup lens 5 again, and is guided by the color separation prism 7 to the image sensing element 7r which receives red and infrared light.

A signal of the image sensing element 7r is converted into a video signal by the amplifying circuit 21r, and is inputted into the image board 22 further to be displayed on the television monitor 27 through the image control means 25. A camera person observes the fundus image displayed on this television monitor 27 to perform the check of a sensed portion, and the like. When the brightness of this fundus image is not suitable, the camera person operates the observation light intensity adjustment knob 32. Since the amount of a current which flows into the observation light sources 16a to 16f is adjusted according to the operation of this knob 32 and luminescence intensity changes, the camera person can observe the fundus image in suitable brightness.

In addition, light emitted by the focus index illumination light source 17 passes through the small opening 15b of the ring diaphragm 15, and the small opening 14b of the crystalline lens diaphragm 14, and permeates the optical path branching mirror 13 to illuminate the slit opening 15d through the deflection prisms 11b and 11c of the focusing unit 11 through the second relay lens 12. An image of the slit opening 11d which is illuminated in this way passes through the black spot plate 10, first relay lens 9, and an opening portion of the cornea diaphragm 8 by an action of the deflection prisms 11b and 11c, and is reflected toward the left by a peripheral mirror portion of the perforated mirror 2 to be projected on the fundus Er of the eye E to be examined through the objective lens 1.

Since the small opening 15b of the ring diaphragm 15 and the perforated mirror 2 are made approximately conjugated with the pupil Ep, all the light outgoing from the small opening 15b is never reflected by the peripheral mirror portion since incident on the opening of the perforated mirror 2 unless the deflection prisms 11b and 11c act. However, the image of the small opening 15b is formed in positions decentered from the optical axis, i.e., an opening position of the perforated mirror 2, as two slit images because of the existence of the deflection prisms 11b and 11c.

Figure 8:
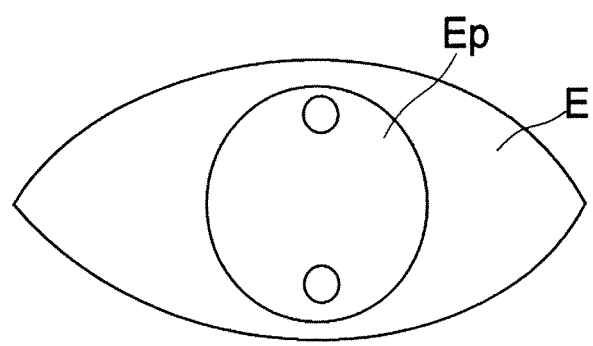
FIG. 8 is an explanatory drawing of an incidence position of an optical slit image on a pupil.

In addition, since a right half and a left half of the slit image are deflected in different directions respectively, the image in the small opening 15b is formed in two symmetrical places which sandwich the opening of the perforated mirror 2. Because of this, as shown in FIG. 8, left and right slit images are projected on the fundus Er of eye from the two positions with up-and-down symmetry which sandwich the optical axis on the pupil Ep.

Figure 9A:
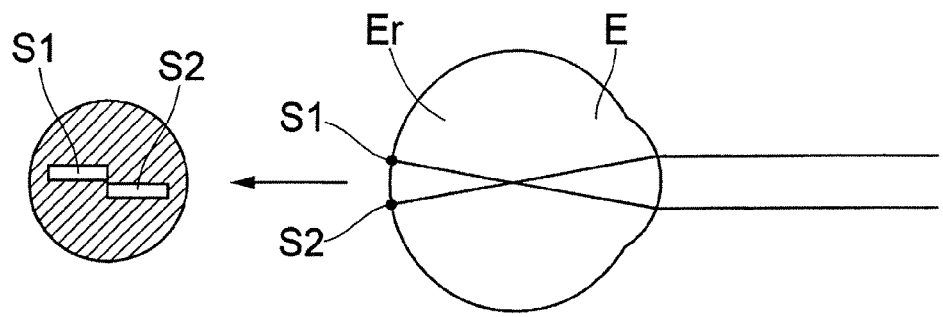
FIGS. 9A, 9B and 9C are explanatory drawings of states that a slit image separates.
Figure 9B:
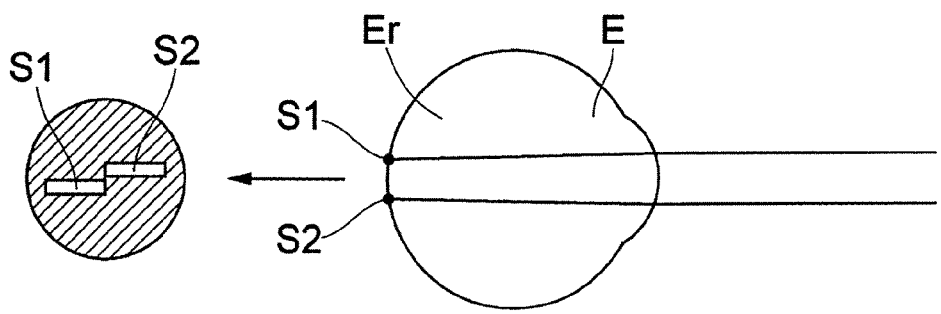
Figure 9C:
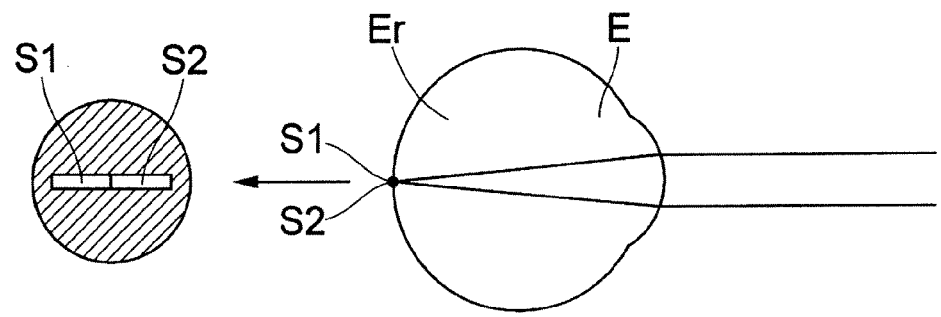

Because of this, as shown in FIGS. 9A and 9B, when the projected positions of the slit images S1 and S2 are shifted from the fundus Er of eye, the slit images S1 and S2 are projected with being separated up and down from each other. In addition, as shown in FIG. 9C, when coinciding with the fundus Er of eye, the slit images S1 and S2 are aligned in a line.

As mentioned above, since the small opening 15b is arranged in the focal position of the second relay lens 12, the light outgoing from the second relay lens 12 is approximately parallel light. Hence, even if the focusing unit 11 moves on the optical axis, a deflected angle is always constant and eccentricity on the pupil Ep is also always constant, and hence, focus precision is not spoiled.

The slit images S1 and S2 which are projected on this fundus Er of eye pass through the pupil Ep, objective lens 1, image sensing diaphragm 3, and focus lens 5 again, and enter into the color separation prism 7 to be guided into the image sensing element 7r. This signal is converted into a video signal by the amplifying circuit 21r, and is inputted into the image board 22 to be displayed on the television monitor 27 with a fundus image. The camera person can perform focus adjustment by operating the focus switch 31 so that these two slit images may be aligned in a straight line.

At this time, when the brightness of a focus index image is not suitable, the brightness adjustment switch 33 of the slit images S1 and S2 is operated. Thereby, since a current flowing in the index illumination light source 17 is adjusted and emitted energy changes, the brightness of the slit images S1 and S2 can be adjusted. Thus, since the observation light sources 16a to 16f and the focus index illumination light source 17 are provided separately, it is possible adequately to adjust also the brightness of the focus index with keeping the brightness of the fundus image suitably. Hence, it is possible to observe always the index image with suitable contrast.

As mentioned above, since the ring diaphragm 15 and the perforated mirror 2 are conjugated approximately, the small opening 15b which is opened on the optical axis of the ring diaphragm 15 is imaged in an opening portion of the perforated mirror 2. That is, the other light than the light which is deflected through the deflection prisms 11b and 11c among the light which outgoes from the index illumination light source 17 and passes through the opening 15b enters into the opening of the perforated mirror 2 and is not reflected in a direction of the objective lens 1. Hence, it does not become ghost light.

If a camera person operates the focus switch 31 as mentioned above so that the slit images S1 and S2 may become in a straight line, the focus lens 4 and focusing unit 11 move in a direction of the optical axis respectively. Then, as shown in FIG. 9C, the slit images S1 and S2 are projected in conjugation on the fundus Er of eye. So long as the left and right slit images S1 and S2 are sensed at the time of being in a straight line, a focused image is obtained since the focus lens 4 is adjusted so that the image sensing elements 7b, 7g, and 7r may keep always conjugation with a focus index projection plane.

Thus, when a camera person operates the sensing switch 29 after image sensing preparation is completed, the CPU 28 detecting this input turns off the observation light sources 16a to 16f and the index illumination light source 17, retreats the focusing unit 11 out of the optical path, sets the amplifying circuits 21r, 21g, and 21b as amplification factors for still image sensing, and turns on the sensing light source 20 with starting the accumulation of the image sensing elements 7b, 7g, and 7r.

The light which is emitted by the sensing light source 20 passes an opening of the ring diaphragm 19, and an opening of the crystalline lens diaphragm 18, and is reflected upward by the optical path branching mirror 13. Then, the light passes through the second relay lens 12, black spot plate 10, first relay lens 9, and an opening portion of the cornea diaphragm 8, and is reflected toward the left in a mirror portion of the perforated mirror 2 to illuminate the fundus Er of eye through the objective lens 1 and pupil Ep.

The fundus image illuminated in this way passes through the pupil Ep, objective lens 1, image sensing diaphragm 3, focus lens 4, and image sensing lens 5 again, and is dispersed into three colors of blue (B), green (G), and red (R) by a spectrum prism 6. Then, three colors are imaged on the image sensing elements 7b, 7g, and 7r respectively to be converted into electric signals, and are converted into digital data by the A/D converter 23 of the image board 22 to be displayed on the television monitor 27 and to be recorded on a recording medium D by the recording means 30. Then, the focusing unit 11 is again arranged in the optical path, the observation light sources 16a to 16f and index illumination light source 17 are turned on, and a series of image sensing operations are ended.

Second Embodiment

Figure 10:
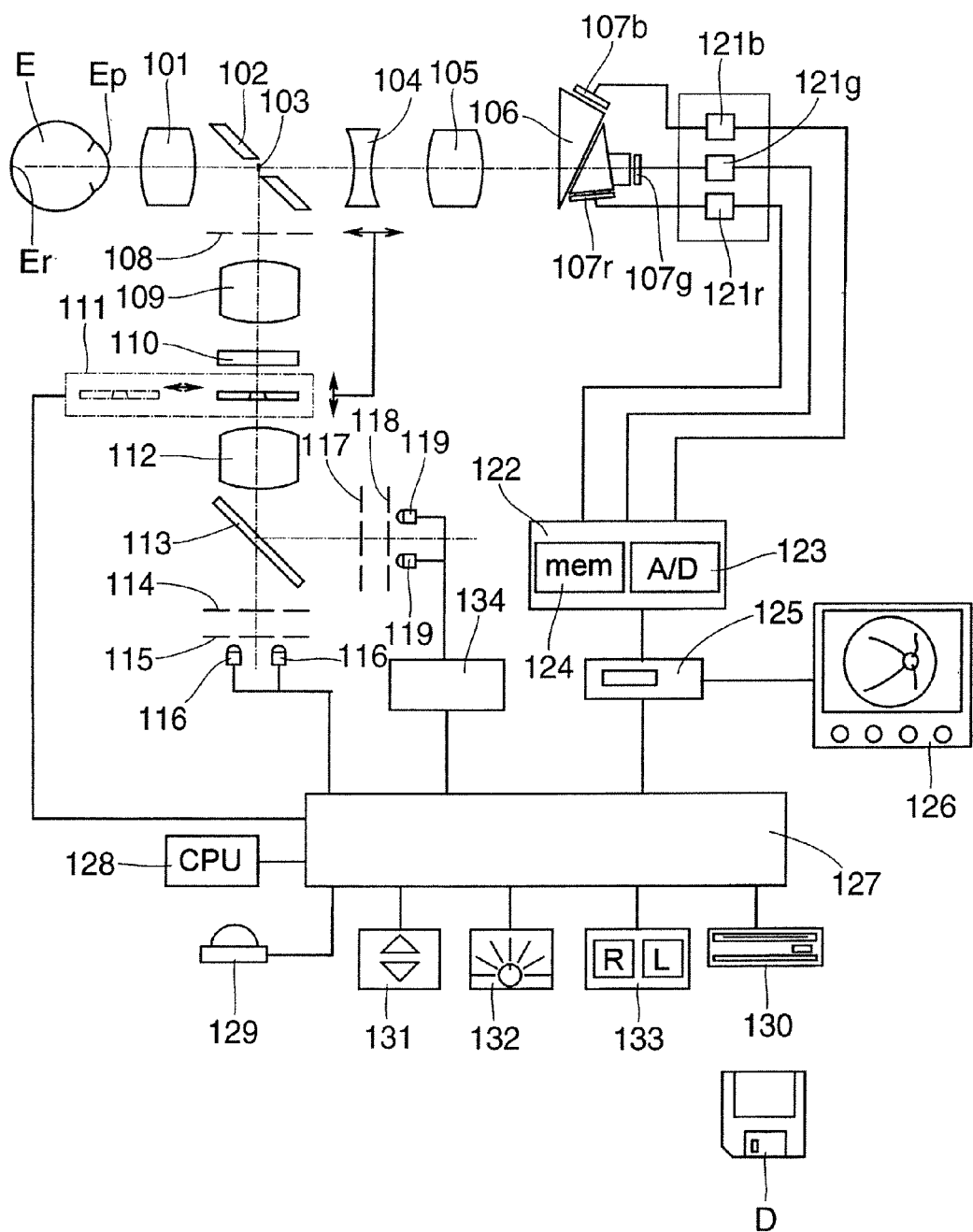
FIG. 10 is a structural diagram of the fundus camera of the first embodiment.

FIG. 10 is a structural diagram of a fundus camera in which the present invention is implemented. Fundus examination and sensing means has the structure that an image sensing mechanism comprising the objective lens 101, perforated mirror 102, image sensing diaphragm 103 arranged inside an opening of this perforated mirror 102, focus lens 104, image sensing lens 105, color separation prism 106, and image sensing devices 107r, 107g and 107b is arranged in front of an eye E to be examined.

Figure 11:
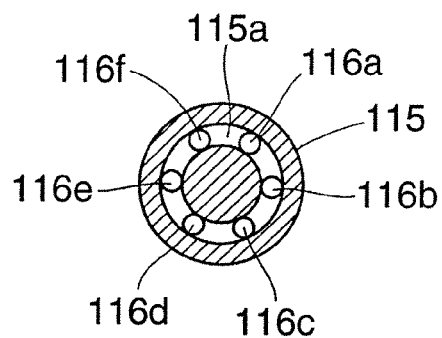
FIG. 11 is a layout drawing of an opening of a ring diaphragm, and LED light sources.

What are arranged in a fundus illumination system in an incident direction of the perforated mirror 102 are in view of the perforated mirror 102 the cornea diaphragm 108 having a ring-like opening projected near a cornea, first relay lens 109, black spot plate 110 on which black spots for removing reflection by the objective lens 101 are formed near an optical axis, fixation target unit 111 which moves in a direction of the optical axis with interlocking with the focus lens 104, and retreats out of an optical path at the time of still image sensing, second relay lens 112, optical path branching mirror 113 which reflects visible light and transmits infrared light, crystalline lens diaphragm 114 having a ring-like opening projected near a rear surface of a crystalline lens of an eye to be examined, ring diaphragm 115 having a ring-like opening 115a projected near a pupil Ep of the eye E to be examined, and observation light sources 116a to 116f which emit infrared light and are arranged circumferentially along the ring-like opening 115a as shown in FIG. 11.

Figure 12:
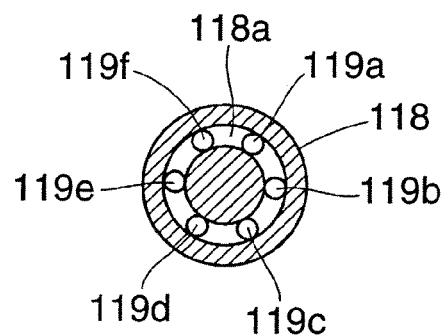
FIG. 12 is a layout drawing of an opening of a ring diaphragm, and visible light sources.

What are arranged In a reflecting direction of the optical path branching mirror 113 are a crystalline lens diaphragm 117 having a ring-like opening projected near the rear surface of the crystalline lens of the eye E to be examined, a ring diaphragm 118 having a ring-like opening 118a projected near a pupil Ep of the eye E to be examined, and visible light sources 119a to 119f for image sensing, such as white LEDs, along an opening 118a as shown in FIG. 12.

Figure 13:
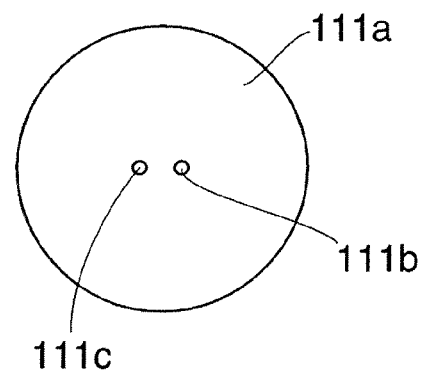
FIG. 13 is a plan of minute openings of an infrared filter.
Figure 14:
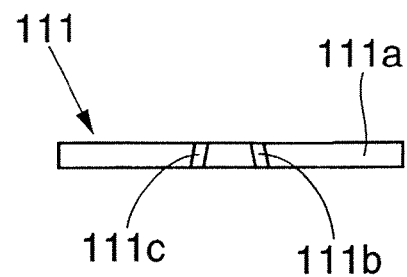
FIG. 14 is a sectional view of the minute openings of the infrared filter.

An optical system portion of the fixation target unit 111 arranged between the first and second relay lenses 109 and 112 is constituted of an infrared filter 111a which transmits visible light and interrupts infrared light. Minute openings 111b and 111c are pierced in a central portion of the filter 111a in positions, which are decentered left-right symmetrically, as shown in FIG. 13. These minute openings 111b and 111c incline in different directions respectively as shown in FIG. 14, and penetrate the filter 111a.

An opening of the perforated mirror 102 is conjugated approximately about the objective lens 101 with an anterior segment of the eye E to be examined, and also focal positions of the first relay lens 109 and second relay lens 112 are approximately conjugated with the anterior segment of the eye E to be examined. Hence, the diaphragm 115 and diaphragm 118 are arranged in the approximately focal position of the second relay lens 112.

Each output of the image sensing elements 107r, 107g, and 107b is connected to the image board 122 through the amplifying circuits 121r, 121g, and 121b. The image board 122 has the A/D converter 123 and memory 124, and its output is connected to the image control means 125, a television monitor 126, and a system bus 127. Furthermore, what are connected to the system bus 127 are the fixation target unit 111, CPU 128, sensing switch 129, recording means 130, a focusing switch 131, an observation light intensity dimmer knob 132, a selecting switch 133 which selects a fixation target presenting position according to the right and left of the eye E to be examined, and a lamp drive circuit 134 to drive the visible light sources 119a to 119f.

In order to sense an image of the fundus Er of eye to be examined using this fundus camera, a camera person sits a person to be examined in front of the fundus camera, and performs the alignment of the eye E to be examined and the fundus camera, and focusing, with observing moving images of the fundus Er of eye of the person to be examined.

The light which is emitted by the LED light sources 116a to 116f passes the ring-like opening 115a of the diaphragm 115, and a ring-like opening of the diaphragm 114, and passes through the optical path branching mirror 113. Then, the light passes through the second relay lens 112, the fixation target unit 111, black spot plate 110, first relay lens 109, and an opening of a diaphragm 108, and is reflected toward the left by the perforated mirror 102 to illuminate the fundus Er of eye through the objective lens 101 and pupil Ep of the eye E to be examined.

A reflected image of the fundus Er of eye illuminated in this way passes through the objective lens 101, image sensing diaphragm 103, focus lens 104, and image sensing lens 105 again, and is guided by the color separation prism 106 to the image sensing element 107r which receives red and infrared light. This signal is converted into a video signal by the amplifying circuit 121r, and is inputted into the image board 122 further to be displayed on the television monitor 126 through the image control means 125.

A camera person observes the fundus image displayed on this television monitor 126 to perform the check of a sensed portion, and the like. When the brightness of this fundus image is not suitable, the camera person operates the observation light intensity dimmer knob 132. Since the amount of a current which flows into the LED light sources 116a to 116f is adjusted according to the operation of this knob 132 and luminescence intensity changes, the camera person can observe the fundus image in suitable brightness.

As shown in FIG. 12, only a light source 119b among the visible light sources 119a to 119f for fixation target presentation arranged circumferentially along the opening 118a of the diaphragm 118 is turned on in stationary light in luminance darker than that at the time of image sensing. Visible light emitted by the light source 119b is reflected upward by the optical path branching mirror 113 through the opening 118a of the diaphragm 118, and illuminates the fixation target unit 111 through the second relay lens 112.

Figure 15:
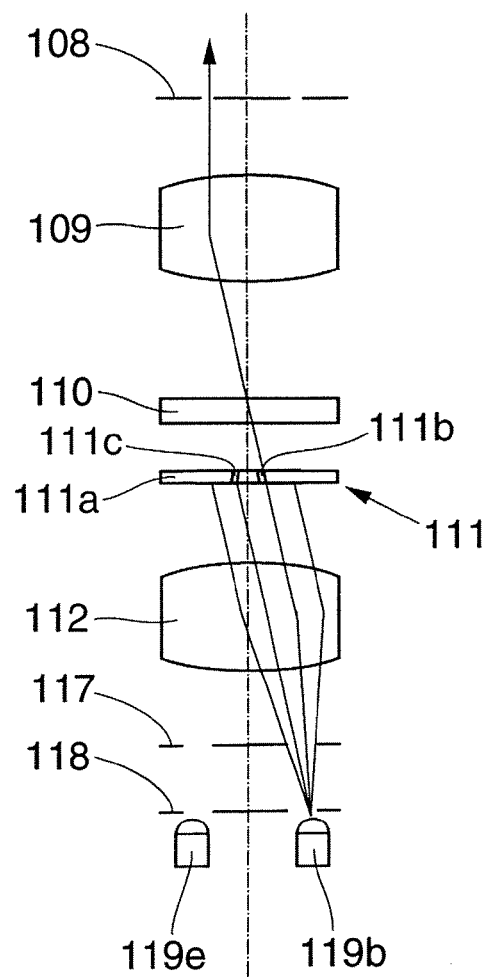
FIG. 15 is an explanatory drawing of luminous flux which passes through a minute opening.

Since the light source 119b is arranged in an approximately focal plane of the second relay lens 112, as shown in FIG. 15, the light which is emitted by the light source 119b becomes parallel light going toward the prism 111a by the second relay lens 112, and all the light progresses with the same inclination. The opening 111b of the filter 111a has an inclination equal to an angle of this light, and the other opening 111c has an inclination which coincides with an angle of the light which is emitted by the light source 119e.

Hence, the light incident on the opening 111b among the light being emitted by the light source 119b permeates the opening 111b, passes through the black spot plate 110, first relay lens 109, and an opening portion of the diaphragm 108, and is reflected toward the left by a peripheral mirror portion of the perforated mirror 102 to be projected on the fundus Er of eye through the pupil Ep. On the other hand, since the light incident on the opening 111c is interrupted by the oblique opening, only an image of the opening 111b is shown to the eye E to be examined as a fixation target for the person to be examined.

Similarly, when the light source 119e turns on, the light which is emitted by the light source 119e becomes parallel light oblique in a direction reverse to the light which is emitted by the light source 119b, by the second relay lens 112 to illuminate the filter 111a. Hence, luminous flux incident on the opening 111c passes this opening 111c, and passes the black spot plate 110, first relay lens 109, and an opening of the diaphragm 108 to reach the fundus Er of the eye E to be examined. But, luminous flux incident on the opening 111b is interrupted by the oblique opening of this opening 111b.

Thereby, a person to be examined can recognize only an image of the opening 111c as a fixation target. That is, it is possible to switch a position of the fixation target by switching the light source 119 to turn on.

In addition, the fixation target unit 111 moves in a direction of the optical axis with interlocking with the focus lens 400 so that an image forming position of the opening 111b or opening 111c which is the fixation target may always coincide with an image sensing plane. Hence, when a camera person operates the focusing switch 131 with looking at the fundus image displayed on the television monitor 126 and focuses on the fundus Er of eye, it is possible to sense always an image of the fixation target with contrast good to the eye E to be examined.

A camera person observes the fundus image displayed on the television monitor 126, and operates the sensing switch 129 after confirming that a person to be examined gazes at the fixation target and image sensing coverage is suitable. The CPU 128 which detects an input into the sensing switch 129 turns off the light sources 116a to 116f, and once turns off the light source 119b to retreat the fixation target unit 111 out of the optical path. While changing amplification factors of the amplifying circuits 121b, 121g, and 121r for still image sensing and starting accumulation, the CPU 128 makes the sensing light sources 119a to 119f emit light for a short time in the luminance for image sensing.

The light which is emitted by the sensing light sources 119a to 119f passes an opening 118a of the diaphragm 118, and an opening of the diaphragm 117, and is reflected upward by the optical path branching mirror 113. Then, the light passes through the second relay lens 112, black spot plate 110, first relay lens 109, and an opening portion of the diaphragm 108, and is reflected toward the left in a mirror portion of the perforated mirror 102 to illuminate the fundus Er of eye through the objective lens 101 and pupil Ep.

The fundus image illuminated in this way passes through the pupil Ep, objective lens 101, image sensing diaphragm 103, focus lens 104, and image sensing lens 105 again, and is dispersed into three colors of blue (B), green (G), and red (R) by the color separation prism 106 to be imaged on the image sensing elements 107b, 107g, and 107r, respectively. Then, the images are converted into electric signals, and are amplified so as to become proper color balance by the amplifying circuits 121b, 121g, and 121r to be converted into digital data by the A/D converter 123. While being displayed on the television monitor 126, the data is recorded on a recording medium D by the record means 130. Then, the fixation target unit 111 is again arranged in the optical path, the light sources 116a to 116f and light source 119b are turned on, and a series of image sensing operations are ended.

Next, when sensing an image of another eye, the right and left eye selecting switch 133 is operated. Then, the CPU 128 which detects an input of the switch 133 turns on the light source 119b or 119e corresponding to a direction selected through the lamp drive circuit 134.

Similarly to the above, when the light source 119b turns on, since the light which is emitted by the light source 119b can pass only through the opening 111b, it is possible to show the image of the opening 111b as the fixation target to a person to be examined.

Although the fixation target presenting positions corresponding to right and left eyes are switched with the selecting switch 133 in the above-mentioned embodiment, the fixation target may be switched on the basis of detected information by detecting the right or left of the eye E to be examined using known detecting means.

Third Embodiment

Figure 16:
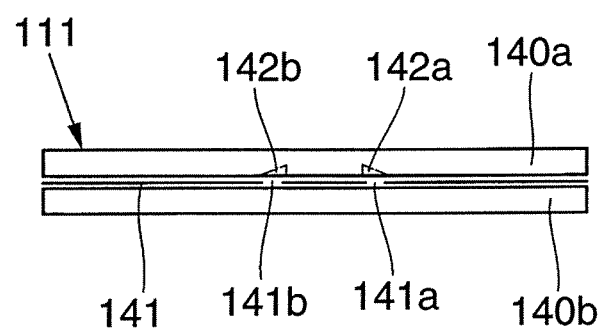
FIG. 16 is a structural diagram of a fixation target unit of a second embodiment.
Figure 17:
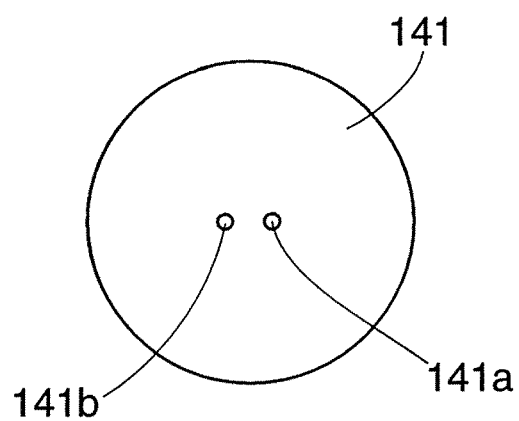
FIG. 17 is a plan of minute openings of an infrared filter.
Figure 18:
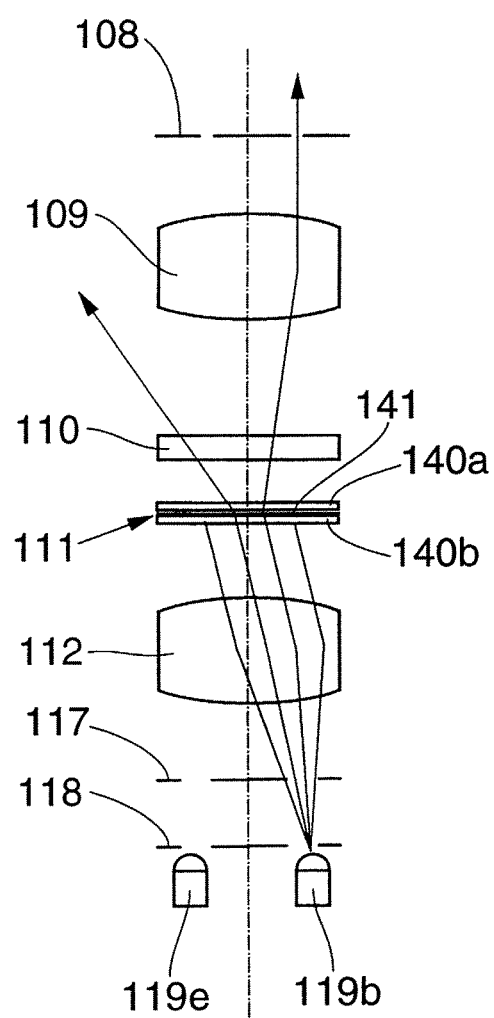
FIG. 18 is an explanatory drawing of luminous flux which passes through the minute openings.

In addition, although the example of using the openings 111b and 111c, which are slantly pierced in the infrared filter 111a as the fixation targets in the fixation target unit 111 of the second embodiment, it is also good to arrange a prism, which deflects an optical path, near an opening used as a fixation target. FIGS. 16, 17 and 18 show the third embodiment in that case.

FIG. 16 is a structural diagram of the fixation target unit 111 which uses prisms, and an infrared filter 141 which transmits infrared light and interrupts visible light is sandwiched between transparent plates 140a and 140b. In this third embodiment, since oblique openings are never provided, a sheet-like low-cost filter is used as the infrared filter 141. In addition, as shown in FIG. 17, openings 141a and 141b are provided near a center of this infrared filter 141 as fixation targets. Prisms 142a and 142b are formed in portions of a transparent sheet 140a which correspond to these openings 141a and 141b.

Thereby, as shown in FIG. 18, the light which is emitted by the light source 119b becomes parallel light with the second relay lens 112 similarly to the second embodiment to illuminate the openings 141a and 141b of the infrared filter 141 through the transparent plate 140b. The luminous flux incident on the opening 141a is deflected at an angle reverse to the optical axis by the prism 142a. This luminous flux passes the first relay lens 109 and the opening of the diaphragm 108 through the black spot plate 110, and proceeds to the peripheral mirror part of the perforated mirror 102. Further, the luminous flux reaches the fundus Er of the eye E to be examined, and the person to be examined can recognize an image of the opening 141a as a fixation target.

On the other hand, the luminous flux incident on the opening 141b is deflected in a direction having an angle larger to the optical axis by the prism 142b. Therefore, this light never enters into the first relay lens 109 after passing through the black spot plate 110. Alternatively, since being interrupted by the diaphragm 108 even if being incident on the first relay lens 109, the light never reaches the fundus Er of eye of a person to be examined.

Thereby, the person to be examined can recognize only the opening 141a as a fixation target. When the light source 119e is turned on, on the contrary, the light incident on the opening 141a is interrupted by being deflected out of the optical path by an action of the prism 142a. The light incident on the opening 141b is deflected in a direction symmetric to the optical axis by an action of the prism 142b, and is projected on the eye E to be examined through the black spot plate 110, first relay lens 109, and the opening of the diaphragm 108.

Hence, when the light source 119e is turned on, a person to be examined can recognize only the opening 141b as a fixation target. Thus, it is possible to show a fixation target according to the right and left of the eye E to be examined by switching the lighting of the light sources 119b and 119e.

Fourth Embodiment

Figure 19:
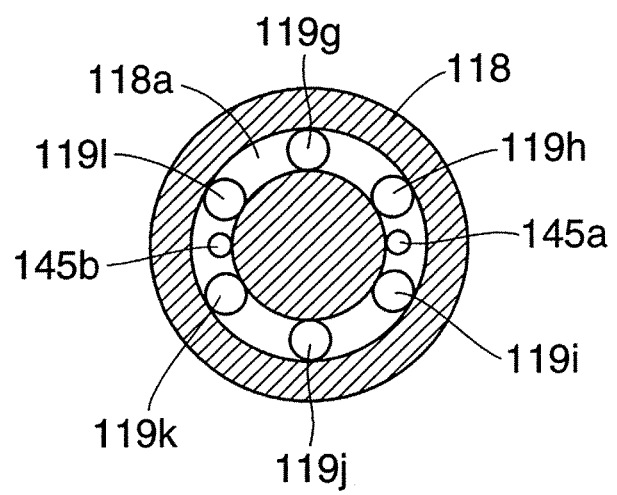
FIG. 19 is a layout drawing of an opening of a ring diaphragm, and light sources of a third embodiment.
Figure 20:
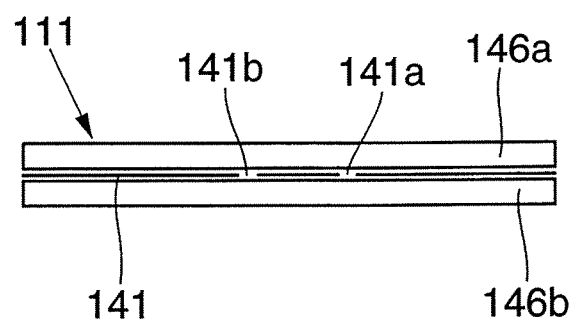
FIG. 20 is a structural diagram of a fixation target unit.
Figure 21:
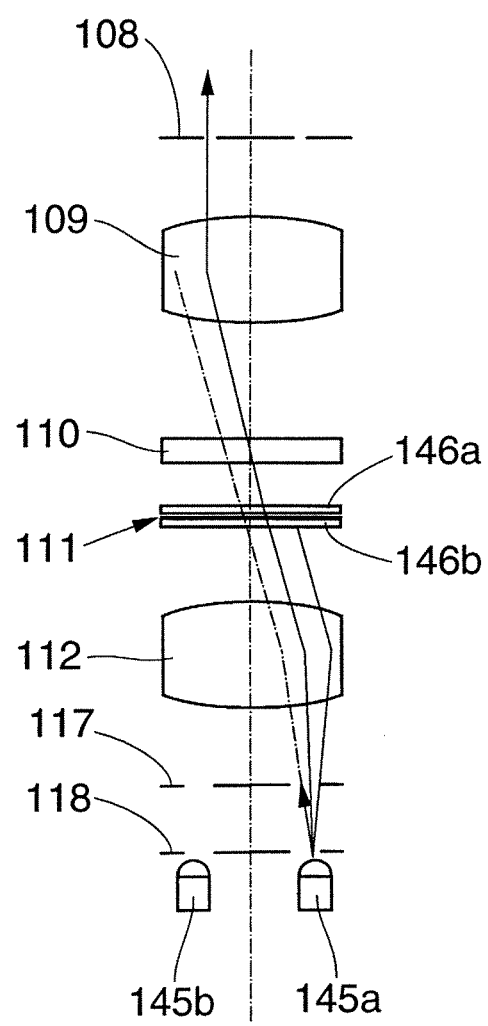
FIG. 21 is an explanatory drawing of luminous flux which passes through a minute opening.

In addition, it is possible to provide a light source for fixation target illumination near a fund illumination light source, and FIGS. 19 and 20 show this fourth embodiment. FIG. 19 shows the arrangement of sensing light sources 119g to 119l on a circumference to the opening 118a of the diaphragm 118. Two light sources 145a and 145b for fixation target illumination are on the same plane as the sensing light sources 119g to 119l, and are arranged nearer to the optical axis than the light sources 119g to 119l.

FIG. 19 is a structural diagram of the fixation target unit 111 of a fourth embodiment. The sheet-like infrared filter 141 in which the minute openings 141a and 141b are formed in symmetric positions near its center similarly to the previous embodiment is sandwiched between the transparent sheets 146a and 146b.

As shown in FIG. 20, the luminous flux which is emitted by the light source 145a passes through the opening 115a of the ring diaphragm 115, and becomes parallel light by the second relay lens 112 further through the opening of the crystalline lens diaphragm 114. The light which illuminates the opening 141a of the infrared filter 141 of the fixation target unit 111 and passes through the opening 141a passes through the transparent plate 143, black spot plate 110, first lens 109, and the opening of the diaphragm 108 to be projected on the fundus Er of the eye E to be examined.

However, since the light which should illuminate the opening 141b is interrupted by a light shielding portion of the diaphragm 118 around the optical axis as shown by a short dashes line in FIG. 20 because the light source 145a is arranged nearer to the optical axis than the light sources 119g to 119l, the opening 141b is never illuminated. Hence, a person to be examined can recognize only an image of the opening 141a as a fixation target.

Similarly, since the light which is emitted by the light source 145b can illuminate the opening 141b, but never illuminates the opening 141a because of being interrupted by the light shielding portion of the diaphragm 118. Thus, it is possible to show a fixation target according to the right and left of the eye E to be examined by switching the lighting of the light sources 145a and 145b.

According to the above embodiment, since it is possible to show a fixation target according to a right or left eye just by selectively turning on a light source in an illumination optical system fixedly arranged. Hence, since it is not necessary to provide a branch optical path, it is possible to downsize an optical system.

In addition, since it is also possible to use a light source, used for image sensing, for the illumination of a fixation target, it is possible to reduce a parts count and to simplify structure.

According to the above-mentioned invention, it is possible to provide an ophthalmic image sensing apparatus which makes it possible to obtain a fundus image with good image quality without illumination unevenness.

As many apparently widely different embodiments of the present invention can be made without departing from the spirit and scope thereof, it is to be understood that the invention is not limited to the specific embodiments thereof except as defined in the claims.

What is clamed is:

1. An ophthalmic image sensing apparatus comprising:
an illumination optical unit configured to illuminate an eye to be examined with infrared light;
a fundus image sensing optical unit configured to sense a fundus image of the eye to be examined;
a focus unit including a base, a slit chart disposed on the base, and at least a deflection prism disposed on the base at a position corresponding to a slit opening in the slit chart, wherein the slit opening is arranged on an optical axis of the illumination optical unit;
a focus index illumination light source configured to illuminate the slit opening; and
a retreating unit configured to retreat the focus unit out of the optical axis of the illumination optical unit in a case that the fundus image sensing optical unit senses the fundus image.

2. An ophthalmic image sensing apparatus according to claim 1, further comprising a light shielding member,
wherein the illumination optical unit is arranged in an opening portion provided near an optical axis on the light shielding member.

3. An ophthalmic image sensing apparatus according to claim 1, wherein the slit chart projects two slit index images on the fundus of the eye to be examined by the at least a deflection prism.

4. An ophthalmic image sensing apparatus according to claim 3, wherein the two slit index images are divided from one slit chart by two deflection prisms.

5. An ophthalmic image sensing apparatus according to claim 1, wherein the illumination optical unit includes an LED.

6. An ophthalmic image sensing apparatus according to claim 5, further comprising an additional LED for fundus illumination, which is arranged around the LED.

7. An ophthalmic image sensing apparatus, comprising:
an illumination optical unit configured to illuminate an eye to be examined;
a fundus image sensing optical unit configured to sense a fundus image of the eye to be examined;
a sensing light source configured to illuminate the eye to be examined at the time of sensing the fundus image of the eye to be examined;
a perforated mirror configured to branch optical paths of the illumination optical unit and the fundus image sensing optical unit;
first and second relay lenses having focal points near an opening of the perforated mirror;
a focus unit including a base, a slit chart dispose on the base, and a deflection prism disposed on the base at a position corresponding to a slit opening in the slit chart, wherein the focus unit is configured to determine whether or not a corresponding slit image is shifted from a fundus of the eye to be examined;
a light shielding member arranged in a nearly focal position of the second relay lens; and
a retreating unit configured to retreat the focus unit out of the optical axis of the illumination optical unit in a case that the fundus image sensing optical unit senses the fundus image, wherein the focus unit is positioned within the illumination optical unit and the slit opening in the slit chart is arranged on an optical axis of the illumination optical unit between the first and second relay lenses, and on an optical path between the sensing light source and the eye to be examined.

8. An ophthalmic image sensing method comprising:
illuminating an eye to be examined with infrared light from an illumination optical unit;
illuminating the eye to be examined with a focus index from a focus unit; and
retreating the focus unit out of an optical axis of the illumination optical unit in a case where a fundus image of the eye to be examined is sensed,
wherein the focus unit includes a base, a slit chart disposed on the base, and a deflection prism disposed on the base at a position corresponding to a slit opening in the slit chart, and
wherein the slit opening is arranged on the optical axis of the illumination optical unit.

9. A non-transitory computer-readable medium storing a computer-executable program which, when executed by a computer, causes the computer to perform an ophthalmic image sensing method comprising:
illuminating an eye to be examined with infrared light from an illumination optical unit;
illuminating the eye to be examined with a focus index using a focus unit; and
retreating the focus unit out of an optical axis of the illumination optical unit in a case where a fundus image of the eye to be examined is sensed,
wherein the focus unit includes a base, a slit chart disposed on the base, and a deflection prism disposed on the base at a position corresponding to a slit opening in the slit chart, and
wherein the slit opening is arranged on the optical axis of the illumination optical unit.

10. An ophthalmic apparatus comprising:
a focus index illumination light source;
an optical member provided on an optical path of an illumination optical system and configured to separate a beam from the focus index illumination light source in a plurality of different directions; and
a control unit configured to retreat the optical member from the optical path of the illumination optical system in accordance with an image sensing signal for sensing an image of an eye to be examined,
wherein the optical member includes a base, a slit chart disposed on the base, and a deflection prism disposed on the base at a position corresponding to a slit opening in the slit chart, and
wherein the slit opening is arranged on the optical path of the illumination optical system.

11. An ophthalmic apparatus according to claim 10, further comprising an observation light source configured to generate observation light for illuminating the eye to be examined through the illumination optical system,
wherein the control unit turns off the observation light source and the focus index illumination light source in accordance with the image sensing signal.

12. An ophthalmic apparatus according to claim 11, wherein the control unit turns on the focus index illumination light source and moves the optical member into the optical path, after sensing the image of the eye to be examined.

13. An ophthalmic apparatus according to claim 10, further comprising:
an image sensing light source configured to generate image sensing light for illuminating the eye to be examined through the illumination optical system; and
an image sensing unit configured to output the image sensing signal,
wherein the control unit retreats the optical member from the optical path, and causes the image sensing light source to generate image sensing light while retreating the optical member, in response to the image sensing signal from the image sensing unit.

14. An ophthalmic apparatus according to claim 11, further comprising an adjusting unit configured to independently adjust the light intensity of the observation light from the observation light source and the light intensity of the beam from the focus index illumination light source.

15. An ophthalmic apparatus according to claim 11,
wherein the observation light source includes a plurality of LEDs arranged circumferentially around the optical axis of the illumination optical system at a substantial center thereof, and
wherein the focus index illumination light source is an LED arranged at a substantial center of the observation light source.

16. An ophthalmic apparatus according to claim 10, further comprising a diaphragm including a first opening provided on the optical axis of the illumination optical system and a ring-shaped second opening,
wherein the focus index illumination light source is arranged on the optical axis of the illumination optical system, and
wherein the beam from the focus index illumination light source passes through the first opening.

17. An ophthalmic apparatus according to claim 10, further comprising:
a first relay lens provided on the illumination optical system and having a substantial focal point at a position of a diaphragm with a ring-shaped opening; and
a second relay lens provided on the illumination optical system and having a substantial focal point at a position of a diaphragm located on an opening of a perforated mirror,
wherein the optical member is located at a position between the first relay lens and the second relay lens.

18. An ophthalmic apparatus according to claim 10,
wherein the optical member includes a plurality of deflection prisms configured to deflect the beam from the focus index illumination light source in a plurality of directions, and
wherein the deflected beams, each of which is obtained by deflecting the beam into the plurality of different directions by the optical member, are emerged through the slit opening.

19. An ophthalmic apparatus comprising:
an focus index illumination light source;
an optical member provided on an optical path of an illumination optical system and configured to separate a beam from the focus index illumination light source in a plurality of different directions; and
a control unit configured to insert the optical member into the optical path of the illumination optical system, after sensing an image of an eye to be examined while the optical member is retreated from the optical path of the illumination optical system,
wherein the optical member includes a base, a slit chart disposed on the base, and a deflection prism disposed on the base at a position corresponding to a slit opening in the slit chart, and
wherein the slit opening is arranged on the optical path of the illumination optical system.

* * * * *